US005847244A

United States Patent [19]

Shibanuma et al.

[11] Patent Number: 5,847,244
[45] Date of Patent: Dec. 8, 1998

[54] METHOD OF PRODUCING 1,1,1,2,2-PENTAFLUOROETHANE, A METHOD OF PRODUCING 2,2-DICHLORO-1,1,1-TRIFLUOROETHANE, AND A METHOD OF PURIFYING 1,1,1,2,2-PENTAFLUOROETHANE

[75] Inventors: Takashi Shibanuma; Yukio Homoto; Satoshi Komatsu; Toshikazu Yoshimura, all of Settsu, Japan

[73] Assignee: Daikin Industries, Ltd., Osaka, Japan

[21] Appl. No.: 23,881

[22] Filed: Feb. 13, 1998

Related U.S. Application Data

[62] Division of Ser. No. 513,755, Sep. 5, 1995, Pat. No. 5,750,809.

[51] Int. Cl.⁶ .......................... C07C 17/08; C07C 19/08; C07C 17/38
[52] U.S. Cl. .......................... 570/169; 570/166; 570/167; 570/168; 570/176; 570/177
[58] Field of Search .................................. 570/166, 167, 570/168, 169, 176, 177

[56] References Cited

U.S. PATENT DOCUMENTS 4,967,023  10/1990  Carmell et al. .......................... 570/168
5,300,710   4/1994  Corbin et al. ........................... 570/168
5,679,876  10/1997  Hub et al. .............................. 570/176

*Primary Examiner*—Alan Siegel
*Attorney, Agent, or Firm*—Armstrong, Westerman, Hattori, McLeland & Naughton

[57] ABSTRACT

A production method in which reaction processes are divided into two regions comprising one reaction region where mainly perohloroethylene is made to react with HF in a vapor phase in the presence of a catalyst and the other reaction region where HCFC-123 ($CF_3CHCl_2$) and/or HCFC-124 ($CF_3CFHCl$) is made to react with HF in a vapor phase in the presence of a catalyst, the former region being kept at a higher pressure and the latter region at a lower pressure during the reaction procedure. By this method it is possible to keep the conversion of perchloroethylene at a high level while securing the life of a catalyst, and it is also possible to raise the selectivity of HFC-125. This is a method of producing HFC-125 in which the content of CFC-115 is lowered to not more than 15 vol % of the total amount of HFC-125 and CFC-115, and then CFC-115 is made to react with hydrogen in the presence of a catalyst. By this method, reaction conditions can be lightened and the absolute amount of by-products also decreased, and the effective purification of HFC-125 can be realized.

11 Claims, No Drawings

METHOD OF PRODUCING 1,1,1,2,2-PENTAFLUOROETHANE, A METHOD OF PRODUCING 2,2-DICHLORO-1,1,1-TRIFLUOROETHANE, AND A METHOD OF PURIFYING 1,1,1,2,2-PENTAFLUOROETHANE

This application is a divisional of Ser. No. 08/513,755 filed Sep. 5, 1995 now U.S. Pat. No. 5,750,809.

A method of producing 1,1,1,2,2-pentafluoroethane, a method of producing 2,2-dichloro-1,1,1-trifluoroethane, and a method of purifying 1,1,1,2,2-pentafluoroethane.

1. Industrial fields where the invention can be utilized

This invention relates to a method of producing 1,1,1,2, 2-pentafluoroethane that is useful as a substitute for freons and is expected to serve as a refrigerant, a method of producing 2,2-dichloro-1,1,1-trifluoroethane, and a method of purifying 1,1,1,2,2-pentafluoroethane.

2. Prior Art 1,1,1,2,2-pentafluoroethane (HFC-125) is expected to be applied as a refrigerant and is also useful as a substitute for freons.

In recent years, under circumstances whereby freons are regulated, the reduction plan for HCFCs has been determined after that of CFCs. At present, HCFC-22 ($CHClF_2$) that is a kind of HCFC, is widely used as a refrigerant. It is therefore useful to determine and produce a substitute for HCFC-22. As its possible substitutes, HFC 32 ($CF_2H_2$), HFC-152a ($CH_3CHF_2$), HFC-143a ($CH_3CF_3$), HFC-134a ($CF_3CH_2F$), and HFC-125 are proposed. This invention relates to a method of producing HFC-125, one of the proposed substitutes.

As production methods of HFC-125, some reactions have been known: fluorination of perchloroethylene (Jap. Pat. Publication No. 17263/1964, U.S. Pat. No. 4766260); fluorination of HCFC-122 (Jap. Pat. Opening No. 172932/1990, Jap. Pat. Opening No. 29940/1992); fluorination of HCFC-123 (Jap. Pat. Opening No. 226927/1992, WO92/16482, EP513823); and reduction of CFC-115 (Jap. Pat. Opening No. 258632/1989). This invention relates to the reaction process of producing HFC-125 by fluorinating perohloroethylene.

As a method of producing HFC-125, it is reported that the fluorination reaction of a perhaloethylene as a starting material, especially perohloroethylene, is conducted at a temperature from 350° to 380° C. in the presence of a ohromium-oxide catalyst (Jap. Pat. Publication No. 17263/1964). In Jap. Pat. Opening No. 178237/1990, reactions have been improved by changing catalysts. According to the improvement, the conversion of perohloroethylene has been raised, but the selectivity of HFC-125 still remains at a low level of about 15%. As shown in WO92/16479, the low selectivity is unchanged even if the catalyst is changed to one based on Zn.

Like this, in reactions using perchloroethylene as a raw material, the conversion of perohloroethylene has been improved. It cannot, however, be sufficiently confirmed at present whether technology to improve the selectivity of HFC-125 together with its conversion has been achieved.

Accordingly, a reaction starting from HCFC-123 (2,2-dichloro-1,1,1-trifluoroethane) has been proposed. In Jap. Pat. Opening No. 226927/1992; it is shown that HCFC-124 (2-chloro-1,1,1,2-tetrafluoroethane) and HFC-125 can be obtained selectively by using a chromium catalyst having an valence number of three or more. In WO92/16482, a reaction with a catalyst mainly comprised of Zn is explained, showing a result of the high selectivity of HCFC-124. In EP513823, a reaction with a chrom-manganese catalyst is attempted. In any case, these proposals are aimed at a high yield of HFC-125 by improving their catalysts.

When HFC-125 is produced, 1-chloro-1,1,2,2,2-pentafluoroethane (CFC-115) is formed as an impurity, for example, in the process of producing HFC-125 by fluorinating perchloroethylene.

Inasmuch as CFC-115 is one of specified freons whose production must be discontinued in 1995, it is necessary to lower the content of CFC-115 as little as possible in the production of HFC-125. There exists a limit, however, in raising the purity of HFC-125 by rectification because HFC-125 and CFC-115 form an azeotrope-like composition.

The reaction itself of reducing CFC-115 to HFC-125 is already known. Jap. Pat. Opening No. 258632/1989 shows that this reaction is conducted by using a catalyst, in which a metal chosen from the platinum and iron groups or from rhenium is carried on active carbon or alumina. Jap. Pat. Opening No. 29941/1992 shows a method to control the formation of excessively reduced products. WO91/05752 shows a method of performing the reaction by changing a kind of catalyst with a catalyst comprised of a metal chosen from Al, Mo, Ti, Ni, Fe, or Co, on a silicon-carbide carrier. A reaction by using a palladium catalyst on a carrier from the alumina group is shown in EP506525.

All these known technologies are aimed at decreasing the formation of excessively reduced products by improving catalysts to attain a high selectivity of HFC-125. Accordingly, severe selection of a catalyst is needed to raise reaction activity (conversion) and the product's selectivity.

OBJECTIVES OF THE INVENTION

A purpose of this invention is to offer an HFC-125 production method that can attain not only a high conversion of perchloroethylene used as a starting material but also a high efficiency in HFC-125 production.

Another purpose of this invention is to offer a method of efficiently producing an HCFC-123 that can be used to produce HFC-125.

A further purpose of this invention is to offer a purification method enabling to produce HFC-125 efficiently and with high selectivity while mitigating the reaction conditions, including the selection of a catalyst in connection with the conversion and selectivity of the reaction.

THE CONSTITUTION OF THE INVENTION

The inventors found that high pressure and high temperature are effective to increase the conversion of perchloroethylene, and that low pressure and high temperature are effective to improve the selectivity of HFC-125. Accordingly, the increase in pressure will exert conflicting effects on the reaction processes of directly producing HFC-125 by fluorinating perchloroethylene. Furthermore, the increase in reaction temperature that is a common condition to improve the yield of HFC-125 has a defect that may cause catalytic deterioration. Under these conditions the inventors ascertained the reaction process for the effective formation of HFC-125, having created this invention.

This invention thus relates to the method of producing 1,1,1,2,2-pentafluoroethane (HFC-125) in which reactions are conducted in two reaction regions. In the first reaction region, mainly perchloroethylene reacts with hydrogen fluoride in a vapor phase in the presence of a catalyst. In the second reaction region, mainly 2,2-dichloro-1,1,1-trifluoroethane (HCFC-123) and/or 2-chloro-1,1,1,2-tetrafluoroethane (HCFC-124) react with hydrogen fluoride in a vapor phase in the presence of a catalyst. The first reaction region is kept at a higher pressure than the second reaction region.

In the reactions of forming HFC-125 by fluorinating perchloroethylene with hydrogen fluoride, the reaction processes of this invention are divided into two reaction regions. One region is where mainly perchloroethylene reacts with HF in a vapor phase in the presence of a catalyst. The other region is where mainly HCFC-123 ($CF_3CHCl_2$) and/or HCFC-124 ($CF_3CFHCl$) react with HF in a vapor phase in the presence of a catalyst. It is characteristic that the first region is kept at a higher pressure and the second region at a lower pressure while the reactions proceed to produce HFC-125($CF_3CF_2H$).

In the production method based on this invention, dividing reaction regions and the difference in their pressure conditions make it possible in the high-pressure stage to keep the conversion of perchloroethylene at a high level by securing the catalyst's life through maintaining a relatively low temperature. Conversely, in the low-pressure stage, it is possible to increase the selectivity of HFC-125 because a reaction can be conducted at a lower pressure by setting its reaction conditions independently from those of the high-pressure stage.

In the fluorination reaction of perchloroethylene, it is first necessary to use a catalyst of high activity to improve the conversion of perchloroethylene. With such a catalyst, increasing the temperature, maintaining a long contact time, raising the mole ratio of HF to perchloroethylene, and increasing the pressure are required further to improve the conversion by changing reaction conditions. As for the conversion of perchloroethylene, maintaining a high-pressure condition will exert an effect on promoting the reaction.

There exist some defects in each of these factors. For example, increasing the temperature will promote the deterioration of catalysts, although this exerts effects on improving not only the conversion of perchloroethylene but on the selectivity of HFC-125. Extension of the contact time will make a reactor large and then necessitate a larger amount of a catalyst. Or if the same reactor is used, it will decrease the volume of reaction gases, resulting in decreasing productivity. Raising the mole ratio will cause an increased amount of unreacted HF to be recovered and will raise the volume of flowing reaction gases. Especially, increasing the reaction pressure will lead to an increase in perchloroethylene conversion, and also to diminution in the selectivity of target HFC-125 what is worse. This will result in a decrease in the yield of HFC-125.

A reaction process that can solve these defects and make the use of the above-mentioned advantages was offered for the first time by this invention. The process is thus divided into two reaction regions where in the first region perchloroethylene reacts with HF in a vapor phase in the presence of a catalyst and in the second region HCFC-123 and/or HCFC-124 react with HF in a vapor phase in the presence of a catalyst. The former region will be kept at high pressure and the latter will be kept at a lower pressure as reactions proceed.

In this case, the conversion of perchloroethylene can be increased by applying high pressure. For instance, when the conversion of perchloroethylene at 5 $kg/cm^2$ is compared with that at atmospheric pressures the ratio is about 1.5 times at 330° C. Pressure in the high-pressure-reaction stage is recommended to be from 3 $kg/cm^2G$ to 30 $kg/cm^2G$, or preferably from 5 $kg/cm^2G$ to 15 $kg/cm^2G$.

Because the purpose of this high-pressure-reaction stage is to form mainly HCFC-123, the temperature increase needed to improve the selectivity of HFC-125 can be avoided. These two factors for temperature diminution will work toward suppressing the deterioration of catalysts. This is a very advantageous point for dividing reaction stages. Moreover, CFC-1111 ($CCl_2=CClF$), CFC-1112a ($CCl_2=CF_2$), and HCFC-122 ($CHCl_2CClF_2$) are acceptable as reaction gases in this reaction stage.

It was meanwhile found that high-pressure conditions suppress the fluorination reactions of HCFC-123 and HCFC-124 and decrease the selectivity of HFC-125. For example, when the conversion of HCFC-123 and the selectivity of HFC-125 at a pressure of 5 $kg/cm^2$ are compared with those at atmospheric pressure, the ratios at 330° C. will be 3:4 and 1:2, respectively.

It is therefore known that lowering reaction pressure is preferable to raising the yield of HFC-125. Moreover, the formation ratio of chlorine containing undesirable by-products, for example, HCFC-133a ($CF_3CH_2Cl$), CFC-114a ($CF_3CFCl_2$), and CFC-115 ($CF_3CF_2Cl$) to the targeted product HFC-125 will diminish under lower-pressure conditions. From these points of view, the process of this invention is highly advantageous. This is because in the low-pressure stage, pressure can be lowered to the level approximating equipment-pressure losses. Pressure in the low -pressure-reaction stage is recommended to be not more than 5 $kg/cm^2$, or preferably to be 1 not more than 3 $kg/cm^2G$.

Furthermore, catalytic deterioration becomes relatively slower in the fluorination of HCFC-123 and thereafter. Accordingly, in the latter reaction stage, reaction temperature can be kept higher than that in non-dividing of the reaction region. This results in the advantage of increasing HFC-125's selectivity. For instance, the selectivity of HFC-125 will be increased by about 2.5 times by raising the temperature of fluorinating HCFC-123 from 330° C. to 350° C.

From the above-mentioned viewpoints, the advantages of dividing reaction stages and of adopting different reaction pressures for each stage are (a) extension of the lifetime a of catalysts as well as (b) increase in yield of HFC-125.

As mentioned above, temperature in the high-pressure-reaction stage is generally lower than in the low-pressure-reaction stage. Proper temperature ranges will range from 200° to 450° C. (preferably from 250° to 400° C.) in the former stage, and from 250° to 500° C. (preferably from 300° to 450° C.) in the latter stage.

The ratio of hydrofluoric acid to the organic compound (mainly perchloroethylene) to be supplied to the high-pressure-reaction stage should be From 2 to 20 in its mole ratio (preferably from 3 to 15). The ratio for the low-pressure-reaction stage should be from 2 to 20 (preferably from 2 to 15). The proper contact time will be from 60 to 7200 in SV for both stages (preferably from 120 to 3600).

Generally known fluorination catalysts are acceptable as catalysts for the reaction (the high-pressure-reaction stage and/or the low-pressure-reaction stage). But even more preferable catalysts are a chromium-oxide catalyst having a surface area of not less than 170 $m^{2/}g$ (see EP514932), a catalyst comprised of chromium oxide having a surface area of not less than 170 $m^2/g$ and at least one element chosen from Ru and Pt (see EP516000), or a catalyst comprised of active alumina and at least one element chosen from Sn, Mo, V, Pb, Ti, Zr, and Ge.

The two reaction stages may be connected directly. It will be more advantageous, however, to have a distillation column between the two stages, That is, if reaction gases flow continuously from the high-pressure-reaction stage to the low-pressure-reaction stage, the HCl formed in the high-pressure-reaction stage, and the unreacted perchloroethylene, are ready directly to flow in the low-pressure-reaction stage maintained at a high temperature. In this case, HCl exerts an adverse effect on the fluorination reaction. Unreacted perchloroethylene causes catalytic deterioration in the low-pressure-reaction stage. If reaction gases continuously flow from the low-pressure-reaction stage to the high-pressure-reaction stage, the amount of HFC-125 formed in the low-pressure-reaction stage decreases in the high-pressure-reaction stage.

Accordingly, the removal of unnecessary gases for reaction by distillation columns (a) between the high- and low-pressure-reaction stages, and (b) after the low-pressure-reaction stage, is considered to be effective to avoid the defects of the continuous inflow of reaction gases. The installation of distillation columns will enable the advantage whereby the ratio of HF to organic compounds—both to be supplied to each reaction stage—can be set independently. From the distillation column in the high- or low-pressure-reaction stages, unreacted raw materials and by-products (for example, CFC-1111, CFC-1112a, HCFC-122, and HCFC-124) can be recycled to corresponding reaction stages.

Although consideration was given to installing two distillation columns as mentioned above, it is of course possible to install only one column. In such a case, the column is used in such a way that each gas in and out the high- and low-pressure-reaction stages is introduced in or discharged from one distillation column. As an instance of use of this technique, the following is practicable. Liquid drawn from an area in the distillation column where the main compound is perchloroethylene is set at a specified pressure by pumping. The pressurized liquid is mixed with additional perchloroethylene and HF, and fed into the high-pressure-reaction stage. During this process the reaction gas is allowed to be vaporized (a) after or (b) before having been mixed.

A reaction gas from the high-pressure-reaction stage is returned into the area of the distillation column where organic compounds are comprised mainly of HCFC-123 and HCFC-124. Although the pressure of the high-pressure-reaction stage is considered to be from three to 30 kg/cm²G, if its minimum pressure is set at higher than the pressure in the distillation column, it is unnecessary to pressurize the reaction gas for its return into the distillation column. This constitutes an equipment advantage.

Furthermore, a gas drawn from an area in the distillation column where organic compounds are comprised mainly of HCFC-123; and/or a gas drawn from an area where organic compounds are comprised mainly of HCFC-124; are mixed to be introduced into the low-pressure-reaction stage after adjusting the content of HF if necessary. In this case, it is better to mix additional HF with the gas drawn from the distillation column after reducing the pressure of the gas. It is unnecessary, however, to continue to adjust the gas pressure. The composition of a gas drawn from the distillation column can be adjusted in accordance with the content of HCFC-124 in the distillation column. Thus, in either reaction stage, even if the product's composition is changed to some extent because of changes in the reaction conditions, the composition of components in the distillation column can be adjusted by this extraction method.

Reaction gases from the low-pressure-reaction stage are pressurized after being liquefied, or in the gas state as they are, or in both states. The gases can then be returned to an area in the distillation column where organic compounds are comprised mainly of HFC-125 and HCFC-124. The ratio of HF to organic materials to be supplied to each reaction stage can be set up independently even if the process is conducted using one distillation column. Thus, even if one distillation column is used, each of the two reaction stages can be operated so as to have practically independent reaction conditions.

From the top of the distillation column, principally HFC-125 and HCl are extracted and sent to the purification process. The recycling of unreacted perchloroethylene is conducted, for instance, by being mixed with HF and reintroduced into the high-pressure-reaction stage after return to the distillation column.

The materials used in both reaction stages, incidentally, are preferably hydrofluoric-acidproof materials. Hastelloy and Inconel are preferable examples.

Furthermore, according to this invention, HFC-125 can be produced by making principally HCFC-123 and/or HCFC-124 react with hydrogen fluoride at low pressure in a vapor phase and in the presence of a catalyst. In this reaction, the pressure had better been kept at not more than 3 kg/cm²G and the temperature at between 250° and 500° C.

As mentioned above, it is desirable to use a chromium-oxide catalyst having a surface area of 170 m²/g or more, a catalyst comprised of chromium oxide having a surface area of 170 m²/g or more, and at least one element chosen from Ru and Pt, or a catalyst comprised of active alumina and at least one element chosen from Sn, Mo, V, Pb, Ti, Zr, and Ge.

Mostly HCFC-123 can be obtained by mainly causing perchloroethylene to react with hydrogen fluoride in a vapor phase in the presence of a catalyst, at a pressure of between 5 kg/cm²G and 15 kg/cm²G, and at a temperature between 200° and 450° C. In this case it is desirable to use the same catalyst as mentioned above.

This invention also relates to a method of purifying HFC-125, in which CFC-115 is removed by being converted to HFC-125 by making a gas mixture which contains 1,1,1,2,2-pentafluoroethane (HFC-125) and 1-chloro-1,1,2,2,2-pentafluoroethane (CFC-115) of not more than 15 volume percent of the total pentafluoroethane react with hydrogen in a vapor phase in the presence of a catalyst.

This invention relates to a method of purifying HFC-125 that characteristically removes the CFC-115 contained in HFC-125 by causing CFC-115 to react with hydrogen in a vapor phase in the presence of a catalyst to convert to HFC-125. Employing the method of this invention, the purification of HFC-125 can be conducted effectively because CFC-115, an impurity, is converted into the target product HFC-125 by vapor-phase reaction.

Compared with the case where CFC-115 is independently reduced to form HFC-125, the method of this invention has the additional characteristics of being able to select inferior conditions (catalysts, temperature, etc.) in activity (conversion) and selectivity. Accordingly, no specific catalyst is required for this reaction, but general reduction catalysts comprised of an element of Group VIII, including palladium and rhodium, can be used.

In the method of this invention, the gas mixture in which HFC-125, a reduction product of CFC-115, is contained in greater quantity than CFC-115 is called the reaction gas. When CFC-115 is reduced independently, 1,1,1,2-tetrafluoro-ethane (HFC-134a) and 1,1,1-trifluoroethane (HFC-143a)—further reduced products than HFC-125—are created as impurities. Accordingly, in the method of this invention, it was predicted that simultaneously while CFC-115 is being reduced to HFC-125, the HFC-125 in the introduced gas is further reduced to create a large quantity of HFC-134a and HFC-143a.

It was found, however, that the hydrogenation reaction of HFC-125 does not easily proceed when HFC-125 alone is reacted with hydrogen. Thus, when HFC-125 is produced by the reaction of CFC-115 and hydrogen, further hydrogenated compounds (HFC-143a, HFC-134a) are produced. When, however, the reaction of HFC-125 and hydrogen is conducted under the same conditions, the formation of further hydrogenated compounds (HFC-143a and HFC-134a) was found to be much lowered.

This means that in the reaction of hydrogen with a gas mixture (in which HFC-125 is a main component and the content of CFC-115 is small), HFC-125 hardly reacts and only CFC-115 is reduced. Elucidating this fact has made available for the first time the ability to eliminate CFC-115 in HFC-125 by reducing the mixture.

According to the method of this invention, inasmuch as HFC-125 is the main component and CFC115 is controlled at not more than 15 volume percent of the total amount of HFC-125 and CFC-115, it is possible to use a catalyst whose selectivity is inferior to that of a catalyst to be used in the reduction reaction of CFC-115 alone. When the proportion of CFC-115/(CFC-115+HFC-125) is not more than 0.15, the absolute amount of by-products becomes not more than 0.15 times that in the reaction of CFC-115 alone because HFC-125 minimally reacts and almost all by-products are caused by CFC-115.

Accordingly, the method of this invention can purify HFC-125 efficiently because when CFC-115 is converted to the target product HFC-125 by vapor-phase reaction, the amount of produced by-products is small and postconversion treatment will be eliminated in such an amount.

When HFC-125 is produced by the reduction of CFC-115, it is indispensable to set up a reaction condition so that a conversion of nearly 100% can be attained. This is because if the conversion is decreased, the diminished portion is directly related to the increase of CFC-115. Simultaneously, conditions are needed to improve the selectivity of HFC-125. Accordingly in this case, severe reaction conditions or catalysts that have excellent activity and selectivity are needed. In the reaction in this invention, the severity of the reaction conditions, including catalysts, can be somewhat lightened because the initial concentration of CFC-115 is low and HFC-125 is hard to react.

This constitutes a great difference between the reaction in this invention and the reduction reaction of CFC-115 alone. Accordingly, inasmuch as catalysts for the reaction have no special restriction in the method of this invention, general-reduction catalysts can be used that are comprised of an element of Group VIII, including palladium and rhodium. Moreover, compared with the case where CFC-115 gas is independently reduced to form HFC-125, the method of this invention can select inferior conditions (catalysts, temperature, etc.) in activity (conversion) and selectivity.

As catalysts for the method of this invention, general-reduction catalysts can be used in which a metal chosen from the elements of Group VIII, including palladium and rhodium, are carried with alumina or active carbon. The selectivity of HFC-125 is increased when an alumina carrier is used. Catalysts whose selectivity is too low are undesirable. It is better to use, for example, a catalyst having not less than 80% selectivity. Furthermore, it is also possible to use a palladium catalyst that is carried on a carrier and added with at least one metal chosen from vanadium and zirconium. It is desirable, however, to use a catalyst and reaction conditions to ensure that the conversion of CFC-115 is 95% or more in the reaction of CFC-115 alone with hydrogen, and that a selectivity of HFC-125 is 80% or more.

In the method of this invention, the content of CFC-115 in the gas mixture of HFC-125 and CFC-115 is preferably less than 15 volume percent. This is necessary to make the most of the above-mentioned advantages. If the content exceeds that value, it would be better to use this method after diminishing the content by purification of the gas mixture.

The amount of hydrogen necessary to reduce CFC-115 to HFC-125 can be changed depending on the reactivity of CFC-115 (CFC-115 content). Generally, the amount of hydrogen is preferably from 0.5 to 1000 at the ratio of $H_2$:CFC-115.

The reaction temperature of CFC-115 with hydrogen in this invention is preferably from 170° to 400° C. If the temperature is too high, excessively reduced products such as HFC-134a ($CF_3CFH_2$) and HFC-143a ($CF_3CH_3$) are output. Especially, the formation of HFC-143a is undesirable because its boiling point is −47.6° C. and is so close to that of HFC-125 (−48.5° C.) that it is very difficult to separate one from the other. Furthermore, if the reaction temperature is too low, the reaction is hard to proceed.

Although HFC-125 is known to be produced by fluorinating perchloroethylene (Jap. Pat. Publication No. 17263/1964), CFC-115 is generally formed as a by-product in this known method. Accordingly, the crude-gas postreaction contains HF and HCl gases. The presence of these gases itself does not always disturb the reaction of CFC-115 and hydrogen in the method of this invention. It is preferable, however, for the process to conduct the reaction after removing these acids. Furthermore, it is more effective from the viewpoint of the process or the product distribution to use gases purified to HFC-125 and CFC-115 as reaction gases, but this composition should not always be followed.

Moreover, in the reaction to produce HFC-125 by the reduction of CFC-115, unreacted CFC-115 exists as an impurity in HFC-125. In such a case, when the content of CFC-115 is not less than 15% of the total amount of CFC-115 and HFC-125, it is better to supply the mixture to this reaction after its rectification.

As mentioned above, when HFC-125 is produced by making the products in the first reaction region (HCFC-123 and/or HCFC-124) react further with HF in the second reaction region, or by making HCFC-123 and/or HCFC124 react with HF, CFC-115 is also output actually as a by-product together with the target product HFC-125 in the second reaction region or postreaction. It is thus desirable for the effective production of HFC-125 to remove the CFC-115 by this invention's purification method. Purification conditions in this case may be the same conditions as mentioned above.

THE POSSIBILITY OF UTILIZING THE INVENTION IN INDUSTRY

As mentioned above, this invention has two reaction regions in producing HFC-125, which is a useful substitute for freons, by fluorinating perchloroethylene. One reaction stage features mainly a reaction of perchloroethylene and HF, conducted in a gas phase in the presence of a catalyst. The other reaction stage comprises principally a reaction of HCFC-123 ($CF_3CHCl_2$) and/or HCFC-124 ($CH_3CFHCl$) with HF, and is conducted in a gas phase in the presence of a catalyst. Inasmuch as the reaction in the former reaction stage is conducted in a high-pressure condition and the reaction in the latter stage in a low-pressure condition, it is possible in the high-pressure-reaction stage to keep the conversion of perchloroethylene higher by high pressure while ensuring catalyst life by a relatively low temperature. In the low-pressure-reaction stage, the selectivity of HFC-125 can also be improved because reaction conditions can be set up independently from those in the high-pressure-reaction stage, making possible a low-pressure reaction.

Furthermore, according to this invention, because HFC-125 is the main component and the amount of CFC-115 is maintained at not more than 15 volume percent of the total amount of HFC-125 and CFC-115, catalysts may be permitted to have less selectivity than those needed for the reduction reaction of CFC-115 alone. This means that reaction conditions can be lightened regarding the conversion of CFC-115 and the selectivity of HFC-125.

Then, inasmuch as almost all by-products are derived from CFC-115 because HFC-125 reacts only minimally, and because the ratio of CFC-115 to (CFC-115+HFC-125) is kept at not more than 0.15, the absolute amount of by-products will be not more than 0.15 times that in CFC-115 alone. Because of this, as well as the fact that CFC-115 is converted to the target product, it is possible effectively to purify HFC-125.

EXAMPLE

This invention will be explained in the following examples with comparative cases. The following examples do not restrict this invention but a variety of modifications will be possible based on their technical concepts.

Example 1

Nine hundred grams of chromium-oxide catalyst having been treated by fluorination (fluorine content 29%) were infused into Reactor A made of Hastelloy 25A. Keeping the pressure in the reactor at 5 kg/cm$^2$, a mixed gas of hydrofluoric acid (24.7 l/min.) and perchloroethylene (1.9 l/min.) was supplied at a temperature of 330° C. The conversion of perchloroethylene was 62% and the selectivity of HCFC-123, HCFC-124, and HFC-125 was 58%, 27%, and 5%, respectively.

Then the produced HCFC-123 (0.68 l/min.) and HF (8.84 l/min.) were introduced into Reactor B made of Hastelloy 25A at atmospheric pressure and at a temperature of 350° C. The reactor was filled in advance with 320 g of chromium oxide catalyst, having been treated by fluorination (fluorine content 29%). In this case the conversion of HCFC-123 was 82% and the selectivity of HCFC-124 and HFC-125 were 34% and 65%, respectively. The yield of HFC-125 was 22%.

Comparative Example 1

When the reaction was conducted under the same conditions as in Example 1, except that the pressure of Reactor B was changed to the same pressure as Reactor A, the conversion of HCFC-123 in Reactor B was 72%, and the selectivity of HCFC-124 and HFC-125 was 54% and 45%, respectively.

The yield of HFC-125 was 11.6%. The yield of HFC-125 was found to be diminished greatly when a high-pressure condition was used in Reactor B.

Comparative Example 2

Nine hundred grams of chromium-oxide catalyst having been treated by fluorination (fluorine content 29%) were infused into Reactor A made of Hastelloy 25A. Maintaining the pressure in the reactor at atmospheric pressure, a mixed gas of hydrofluoric acid (24.7 l/min.) and perchloroethylene (1.9 l/min.) was supplied at a temperature of 330° C. The other conditions were the same as in Example 1.

In this example the conversion of perchloroethylene was 42%. When the pressure in Reactor A was lowered, the conversion of perchloroethylene was found to be diminished.

Example 2

Ten grams of a catalyst (0.5 wt % Pd on active carbon) were infused into a reactor with an inside diameter of 20 mm. Then a gas mixture of CFC-115 and HFC-125 (ratio of CFC-115 to HFC-125 at 3.5:96.5) (4.4 ml/min. at 25° C.) and hydrogen (3.1 ml/min. at 25° C.) were led through the reactor at a temperature of 250° C.

In this example the conversion of CFC-115 was 97.5% and the proportion of CFC-115/HFC-125 were decreased from 3.63% to 0.0876%. Neither HFC-143a nor HFC-134a were detected.

Example 3

When a reaction was conducted in the same manner as in Example 2 except that a gas mixture of CFC-115 and HFC-125 (ratio of CFC-115 to HFC-125 at 3.5:96.5) (8 ml/min. at 25° C.), and hydrogen (40 ml/min. at 25° C.) were flowed, the conversion of CFC-115 was 99% and the percentage of CFC-115 to HFC-125 was decreased from 3.63% to 0.036%. No HF G-143a was detected.

Example 4

HFC-125 and hydrogen were led at a temperature of 250° C. through 10 g of a catalyst (0.5 wt % Rh on active carbon) infused into a reactor with an inside diameter of 20 mm, at a rate of 20 ml/min. (at 25° C.) and 100 ml/min. (at 25° C.), respectively.

The conversion of HFC-125 was 0.032%. The composition of HFC-125, HFC-143a, and HFC-134a in the produced gas was 99.968%, 0.00%, and 0.032%, respectively. The percentages of HFC-143a and HFC-134a to HFC-125 were 0.00% and 0.0324%, respectively.

Comparative Example 3

A reaction was conducted in the same manner as in Example 4 except that CFC-115 was led instead of HFC-125.

In this case, the conversion of CFC-115 was 20.8% and the selectivity of HFC125, HFC-143a, and HFC-134a were 83.6%, 7.74,%, and 8.4%, respectively. The percentages of HFC-143a and HFC-134a to HFC-125 were 9.26% and 10.04%, respectively.

Whereas HFC-143a and HFC-134a, both excessively reduced products, were formed together with HFC-125 in the reduction reaction of CFC-115, it was found that in the reduction reaction of HFC-125 (Example 4), HFC-125 was hard to be reduced. HFC-143a and HFC-134a were thus minimally formed as compared with the reduction of CFC-115.

Example 5

HCFC-123 (52 ml/min.), HCFC-124 (14 ml/min.), and HF (520 ml/min.) were introduced into a reactor made of Hastelloy 25A filled with 40 g of fluorination-treated chromium-oxide catalyst (fluorine content 29%) at atmospheric pressure and at a temperature of 340° C. The composition ratio of HCFC-123, HCFC-124, and HFC-125 in the produced gas was 2.5:11.4:86.1. The amount of produced HFC-125 was 86.1% of the introduced organic gases.

Example 6

When the outflow gas from Reactor B in Example 1 was purified, the components of the purified gas were CFC-115 and HFC-125. The proportion of CFC-115 to HFC-125 was 1,230 ppm. When this purified gas (8.5 ml/min.) and hydrogen (8.5 ml/min.) were led through a reactor with an inside diameter of 20 mm filled with 10 g of a catalyst (5% Rh on active carbon) at a temperature of 200° C., the conversion of CFC-115 was 99.73% and the composition of the outflow organic gases was 99.993% of HFC-125, 3.3 ppm of CFC-115, 30 ppm of HFC-143a, and 37 ppm of HFC-134a.

What is claimed:

1. A method of producing 1,1,1,2,2-pentafluoroethane, in which 1-chloro-1,1,2,2,2-pentafluoroethane is removed by being converted to 1,1,1,2,2-pentafluoroethane by making a gas mixture of 1,1,1,2,2-pentafluoroethane and 1-chloro-1,1,2,2,2-pentafluoroethane, in which the content of 1-chloro-1,1,2,2,2-pentafluoroethane is not more than 15 vol % of the total amount of these pentafluoroethanes, react with hydrogen in a vapour phase in the presence of a catalyst, in which reactions are conducted in regions comprising the first reaction region wherein mainly perchloroethylene reacts with hydrogen fluoride in a vapor phase in the presence of a catalyst, and the second reaction region wherein mainly 2,2-dichloro-1,1,1-trifluoroethane and/or 2-chloro-1,1,1,2-tetrafluoroethane reacts with hydrogen fluoride in a vapor phase in the presence of a catalyst, said first reaction region being kept at a higher pressure than said second reaction region, and the content of 1-chloro-1,1,2,2,2-pentafluoroethane in the product gas of the reaction region is lowered to not more than 15 vol % by the rectification or extractive rectification, and the resulting gas is used as the gas mixture.

2. A production method as defined in claim 1, in which the pressure in the first reaction region with higher pressure is between 3 kg/cm$^2$G, and 30 kg/cm$^2$G, and the pressure in the second reaction with lower pressure is not more than 5 kg/cm$^2$G.

3. A production method as defined in claim 1, in which the pressure in the first reaction region with higher pressure is between 5 kg/cm$^2$G and 15 kg/cm$^2$G, and the pressure in the second reaction region with lower pressure is not more than 3 kg/cm$^2$G.

4. A production method as defined in claim 1, in which a common distillation column is installed between the first and second reaction regions to ensure that the raw and produced gases of each reaction region enter and leave the column.

5. A production method as defined in claim 4, in which gases drawn from a part comprised mainly of perchloroethylene in the distillation column and hydrogen fluoride are introduced into the first reaction region under higher pressure, and then all or a part of the reacted gases from said first reaction region are returned to said distillation column, gases drawn from a part comprised mainly of 2,2-dichloro-1,1,1-trifluoroethane and/or mainly of 2-chloro-1,1,1,2-tetrafluoroethane in said distillation column are introduced into the second reaction region under lower pressure after being supplemented with hydrogen fluoride, if necessary, then reacted gases from said second reaction region are pressurized after all or part of them are liquefied, or in the gas state as they are, or in both states, and returned to said distillation column, while a gas containing 1,1,1,2,2-pentafluoroethane is drawn from said distillation column.

6. A production method as defined in claim 4, in which the pressure in the first reaction region with higher pressure in greater than that in the distillation column.

7. A production method as defined in claim 1, using a chromium-oxide catalyst having a surface area not less than 170 m$^2$/g, a catalyst comprised of chromium oxide with a surface area not less than 170 m$^2$/g and at least one element selected from Ru and Pt, or a catalyst comprised of active alumina and at least one element selected from Sn, Mo, V, Pb, Ti, Zr, and Ge in the first and/or the second reaction regions.

8. A production method as defined in claim 1, in which the temperature in the first reaction region with high pressure is between 200° and 450° C., and the temperature in the second reaction region with low pressure is between 250° C. and 500° C.

9. A production method as defined in claim 1, in which independent distillation columns are installed before and behind the second reaction region with low pressure.

10. A production method as defined in claim 9, in which the operations are conducted wherein all or a part of the reacted gases from the first reaction region with high pressure are introduced into the first distillation column that is installed in front of the second reaction region, gases are then drawn from an area in said first distillation column where organic compounds are comprised mainly of 2,2,-dichloro-1,1,1-trifluoroethane and/or of 2-chloro-1,1,1,2-tetrafluoroethane to be introduced into said second reaction region after adding hydrogen fluoride, if necessary, gases drawn from an area where organic compounds are mainly comprised of perchloroethylene are introduced with additional perchloroethylene into said first reaction region in a gas condition after HF is added, if necessary, all or a part of the reacted gases from said second reaction region are introduced into the second distillation column, gases are then drawn from an area in the distillation column where organic compounds are mainly comprised of 1,1,1,2,2-pentafluoroethane, while gases drawn from an area where the organic compounds are mainly 2,2-dichloro-1,1,1-trifluoroethane and/or 2-chloro-1,1,1,2-tetrafluoroethane are returned to said second reaction region after hydrogen fluoride is added, if necessary.

11. A production method as defined in claim 10, in which the pressure in the first reaction region with higher pressure is greater than that in the distillation columns.

* * * * *